US009175595B2

(12) United States Patent
Ceynow et al.

(10) Patent No.: US 9,175,595 B2
(45) Date of Patent: Nov. 3, 2015

(54) ENGINE WITH ENGINE OIL VISCOSITY CONTROL AND METHOD FOR CONTROLLING THE SAME

(75) Inventors: Kenneth P. Ceynow, Oak Lawn, IL (US); Frank J. Karlovsky, Bloomingdale, IL (US)

(73) Assignee: International Engine Intellectual Property Company, LLC., Lisle, IL (US)

( * ) Notice: Subject to any disclaimer, the term of this patent is extended or adjusted under 35 U.S.C. 154(b) by 0 days.

(21) Appl. No.: 13/642,999

(22) PCT Filed: Apr. 23, 2010

(86) PCT No.: PCT/US2010/032185
§ 371 (c)(1),
(2), (4) Date: Oct. 23, 2012

(87) PCT Pub. No.: WO2011/133164
PCT Pub. Date: Oct. 27, 2011

(65) Prior Publication Data
US 2013/0180478 A1 Jul. 18, 2013

(51) Int. Cl.
*F01P 7/14* (2006.01)
*F01M 5/00* (2006.01)
*G01N 11/00* (2006.01)

(52) U.S. Cl.
CPC *F01P 7/14* (2013.01); *F01M 5/005* (2013.01); *F16N 2200/12* (2013.01); *G01N 11/00* (2013.01)

(58) Field of Classification Search
CPC ... F01M 1/16; F01M 11/10; F01M 2011/148; F01M 5/001; F01M 11/12; F01M 1/10; F01M 2011/146; F01M 2011/1473; F01M 5/021; F01M 11/0004; F01M 2250/60; F01M 5/005; F01M 1/18; F01M 2011/0045; F01M 2011/14; F01P 2060/04; F01P 11/08; F01P 2060/08; F01P 3/20; F01P 2007/146; F01P 2025/40; F01P 7/16; F01P 2003/006
USPC ................ 123/41.08, 41.33, 196 R, 196 AB; 701/101–104, 29.4, 29.5, 29.1; 73/114.31, 114.32, 114.33, 114.37
See application file for complete search history.

(56) References Cited

U.S. PATENT DOCUMENTS

| 4,180,032 | A | * | 12/1979 | Plegat | 123/563 |
| 4,815,431 | A | * | 3/1989 | Yorita et al. | 123/196 AB |
| 4,955,352 | A | * | 9/1990 | Takeda | 123/559.1 |
| 5,159,910 | A | * | 11/1992 | Ninomiya et al. | 123/196 AB |
| 5,604,441 | A | * | 2/1997 | Freese et al. | 324/663 |
| 5,896,841 | A | * | 4/1999 | Nemoto et al. | 123/381 |

(Continued)

*Primary Examiner* — Lindsay Low
*Assistant Examiner* — Long T Tran
(74) *Attorney, Agent, or Firm* — Jeffrey P. Calfa; Mark C. Bach

(57) ABSTRACT

An engine oil system for an internal combustion engine comprises an electronic control module, an oil viscosity sensor, am engine oil cooler, and an oil cooler flow control valve. The oil viscosity sensor is disposed in communication with the electronic control module. The electronic control module determines a viscosity of oil within the engine oil system based upon an output of the oil viscosity sensor. The oil cooler flow control valve is disposed in communication with the electronic control module. The oil cooler flow control valve is positionable between an open and closed position to regulate coolant flow to the engine oil cooler based upon an output of the electronic control module. The electronic control module moves the oil cooler flow control valve based upon the determined viscosity of the oil.

9 Claims, 1 Drawing Sheet

(56) References Cited

U.S. PATENT DOCUMENTS

| | | | |
|---|---|---|---|
| 6,374,783 B1* | 4/2002 | Toriumi | 123/90.11 |
| 6,434,512 B1* | 8/2002 | Discenzo | 702/184 |
| 7,581,434 B1* | 9/2009 | Discenzo et al. | 73/53.01 |
| 8,046,126 B2* | 10/2011 | Yanagida et al. | 701/31.7 |
| 2003/0005751 A1* | 1/2003 | Berndorfer et al. | 73/54.01 |
| 2004/0211246 A1* | 10/2004 | Han et al. | 73/53.05 |
| 2011/0000188 A1* | 1/2011 | Pegg et al. | 60/273 |
| 2011/0172966 A1* | 7/2011 | Albsmeier et al. | 702/183 |
| 2011/0253092 A1* | 10/2011 | Springer et al. | 123/196 R |
| 2012/0180456 A1* | 7/2012 | Yamada et al. | 60/274 |

* cited by examiner

ENGINE WITH ENGINE OIL VISCOSITY CONTROL AND METHOD FOR CONTROLLING THE SAME

TECHNICAL FIELD

The present disclosure relates to an engine having an engine oil viscosity sensor, and more particularly to an engine having an engine oil viscosity sensor that is utilized to control an engine oil cooler to modify the viscosity of the engine oil.

BACKGROUND

Engine oil, sometimes also referred to as engine lubrication oil or engine lube oil, is continuously fed from an oil rail, or oil gallery to engine parts needing lubrication. For example, it is typically necessary to lubricate parts such as crank shaft and connecting rod bearings, turbochargers and, in some engines, piston cooling jets. An engine oil system is additionally often provided with an engine oil cooler to control the temperature of the engine oil. As engine oil temperature increases, the viscosity of the engine oil decreases, that is the viscosity number of the engine oil decreases, and the engine oil becomes thinner. When the viscosity of the oil is lower, friction between lubricated parts is reduced, but engine durability may be reduced if the viscosity of engine oil becomes too low. Similarly, when the viscosity of the oil is higher, friction between lubricated parts is higher, but engine durability may be increased. Thus, an optimum engine oil viscosity may be determined based upon engine operating conditions that offers a proper balance of limiting friction between lubricated parts, and offering acceptable engine durability. Therefore, a need exists for an engine oil system that monitors engine oil viscosity, and controls the temperature of the engine oil to adjust the engine oil viscosity to a predetermined level based upon engine operating conditions.

SUMMARY

According to one embodiment, an engine oil system for an internal combustion engine comprises an electronic control module, an oil viscosity sensor, an engine oil cooler, and an oil cooler flow control valve. The oil viscosity sensor is disposed in communication with the electronic control module. The electronic control module determines a viscosity of oil within the engine oil system based upon an output of the oil viscosity sensor. The oil cooler flow control valve is disposed in communication with the electronic control module. The oil cooler flow control valve is positionable between an open and closed position to regulate coolant flow to the engine oil cooler based upon an output of the electronic control module. The electronic control module moves the oil cooler flow control valve based upon the determined viscosity of the oil.

According to one process, a method of controlling viscosity of oil within an engine oil system is provided. Oil viscosity is measured with an oil viscosity sensor. An electronic control module monitors engine performance. A target oil viscosity is generated with the electronic control module based upon the monitored engine performance. Oil is provided to an oil cooler. The oil cooler adjusts the temperature of the oil and thereby adjusts viscosity of the oil. An oil cooler flow control valve position is adjusted between an open position and a closed position based upon the measured oil viscosity, the generated target oil viscosity, and the monitored engine performance. The oil cooler flow control valve regulates coolant flow to the oil cooler.

According to another embodiment, an engine oil system for an internal combustion engine comprises an electronic control module, an oil viscosity sensor, an oil flow control valve, and an engine oil cooler. The oil viscosity sensor is disposed in communication with the electronic control module. The electronic control module measures a viscosity of oil within the engine oil system based upon an output of the oil viscosity sensor. The oil flow control valve is disposed in communication with the electronic control module. The oil flow control valve is movable between an open and closed position to regulate oil flow within the engine oil system based upon an output of the electronic control module. The engine oil cooler is disposed downstream of the oil flow control valve. The engine oil cooler receives coolant to remove heat from oil passing through the engine oil cooler. The flow of oil to the engine oil cooler is controlled by the oil flow control valve. The electronic control module moves the oil flow control valve based upon viscosity of the oil.

DETAILED DESCRIPTION

Figure 1:
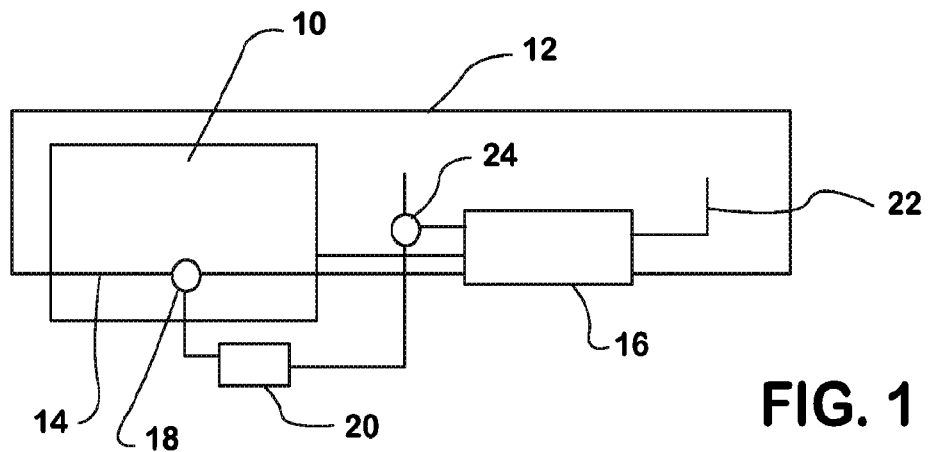
FIG. 1 is a schematic diagram showing an engine and a portion of the engine oil system for an engine having a viscosity sensor and an electronically controlled engine oil coolant flow control valve.

FIG. 1 shows an engine 10 having an engine oil system 12 for a diesel engine. The engine oil system 12 comprises a main engine oil gallery 14 and an engine oil cooler 16. The engine oil system 12 additionally comprises flow paths (not shown) that are in fluid communication with the main engine oil gallery 14 to deliver engine oil to lubricated components of the engine 10.

An engine oil viscosity sensor 18 is disposed within the main engine oil gallery 14. The engine oil viscosity sensor 18 is disposed in communication with an electronic control module (ECM) 20. The engine oil viscosity sensor 18 generates an output indicative of viscosity of engine oil within the engine oil system 12. The ECM 20 contains a memory having predetermined engine oil viscosity settings based on engine 10 operating parameters. The engine 10 operating parameters may include engine torque output, engine oil temperature and oil cooler coolant temperature. The predetermined engine oil viscosity setting is adapted to balance reduction in friction of lubricated engine components from engine oil with high viscosity, and durability based upon engine oil with a low viscosity.

The engine oil cooler 16 is provided with coolant from a coolant system 22. The coolant system 22 has an oil cooler flow control valve 24 disposed therein. The oil cooler flow control valve 24 is in communication with the ECM 20. The oil cooler flow control valve 24 has an open position to allow coolant to flow within the coolant system 22 to the engine oil cooler 16, and a closed position that prevents coolant from flow within the coolant system 22 to the engine oil cooler 16. The oil cooler flow control valve 24 may be positioned anywhere between the open position and the closed position to regulate flow within the coolant system 22 to the engine oil cooler 16. The ECM 20 controls the position of the flow control valve 24.

The ECM 20 compares the output of the engine oil viscosity sensor 18 with the predetermined engine oil viscosity settings to determine if the measured engine oil viscosity needs to be raised or lowered to match the predetermined engine oil viscosity setting. The ECM 20 may contain a memory comprising a look-up table of predetermined engine oil viscosity settings based upon engine operating parameters.

If the measured engine oil viscosity is above the predetermined engine oil viscosity setting, the ECM 20 generates an output that causes the oil cooler flow control valve 24 to move towards the closed position, thereby increasing the temperature of the coolant within the engine oil cooler 16 and, in turn, lowering the viscosity of the engine oil within the engine oil system 12.

Conversely, if the measured engine oil viscosity is below the predetermined engine oil viscosity setting, the ECM 20 generates an output that causes the oil cooler flow control valve 24 to move towards the open position, thereby decreasing the temperature of the coolant within the engine oil cooler 16 and, in turn, raising the viscosity of the engine oil within the engine oil system 12.

Figure 2:
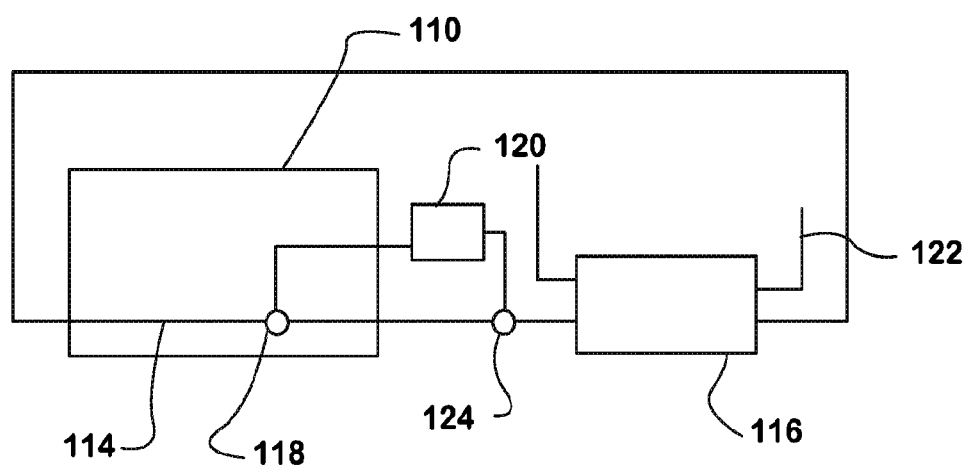
FIG. 2 is a schematic diagram showing an engine and a portion of the engine oil system for an engine having a viscosity sensor and an electronically controlled engine oil flow control valve.

FIG. 2 shows an engine 110 having an engine oil system 112 for a diesel engine. The engine oil system 112 comprises a main engine oil gallery 114 and an engine oil cooler 116. The engine oil system 112 additionally comprises flow paths (not shown) that are in fluid communication with the main engine oil gallery 114 to deliver engine oil to lubricated components of the engine 110.

An engine oil viscosity sensor 118 is disposed within the main engine oil gallery 114. The engine oil viscosity sensor is disposed in communication with an electronic control module (ECM) 120. The engine oil viscosity sensor 118 generates an output indicative of viscosity of engine oil within the engine oil system 112. The ECM 120 contains a memory having predetermined engine oil viscosity settings based on engine 110 operating parameters. The engine 110 operating parameters may include, engine torque output, engine oil temperature, oil cooler coolant temperature. The predetermined engine oil viscosity setting is adapted to balance reduction in friction of lubricated engine components from engine oil with high viscosity, and durability based upon engine oil with a low viscosity.

The engine oil system 112 further comprises an oil flow control valve 124. The engine oil flow control valve 124 is disposed within the engine oil system 112, and is adapted to control an amount of engine oil within the engine oil system 112 that enters the engine oil cooler 116. The oil flow control valve 124 is in communication with the ECM 120. The oil flow control valve 124 has an open position to allow engine oil to flow to the engine oil cooler 116, and a closed position that prevents engine oil from flowing to the engine oil cooler 116. The oil flow control valve 124 may be positioned anywhere between the open position and the closed position to regulate flow of engine oil to the engine oil cooler 116. The ECM 20 controls the position of the oil flow control valve 124. It is contemplated that an engine oil cooler 116 bypass flow path (not shown) may be provided in order to maintain fluid flow within the engine oil system 112 so as not to cause the oil flow control valve 124 to have an undue effect on oil pressure within the engine oil system.

The engine oil cooler 116 is provided with coolant from a coolant system 122 to remove heat from the engine oil passing through the engine oil cooler 116.

The ECM 120 compares the output of the engine oil viscosity sensor 118 with the predetermined engine oil viscosity settings to determine if the measured engine oil viscosity needs to be raised or lowered to match the predetermined engine oil viscosity setting.

If the measured engine oil viscosity is above the predetermined engine oil viscosity setting, the ECM 120 generates an output that causes the engine oil flow control valve 124 to move towards the closed position, thereby increasing the temperature of the engine oil, in turn, lowering the viscosity of the engine oil within the engine oil system 112.

Conversely, if the measured engine oil viscosity is below the predetermined engine oil viscosity setting, the ECM 120 generates an output that causes the engine oil flow control valve 124 to move towards the open position, thereby decreasing the temperature of the engine oil, and, in turn, raising the viscosity of the engine oil within the engine oil system 112.

What is claimed is:

1. An engine oil system for an internal combustion engine having varying engine operating parameters, the engine oil system comprising:
   an electronic control module which contains a memory having predetermined target engine oil viscosity settings which target oil viscosities vary over time based on engine operating parameters;
   an oil viscosity sensor disposed in communication with the electronic control module and which generates an output indicative of the actual viscosity of the oil within the engine;
   an engine oil cooler;
   an oil cooler flow control valve disposed in communication with the electronic control module, the oil cooler flow control valve being moveable between an open and closed position to regulate coolant flow to the engine oil cooler based upon an output of the electronic control module; and
   the electronic control module programmed to:
   compare the output of the engine oil viscosity sensor with the varying target oil viscosity generated by the electronic control module;
   generate an output that causes the oil cooler flow control valve to move towards the closed position during those times when the output of the engine oil viscosity sensor exceeds the target oil viscosity, thereby increasing the temperature of the coolant within the engine oil cooler and, in turn, lowering the viscosity of the engine oil within the engine oil system to lower the actual oil viscosity toward the target oil viscosity; and
   generate an output that causes the oil cooler flow control valve to move towards the open position during those times when the output of the engine oil viscosity sensor is below the target oil viscosity, thereby decreasing the temperature of the coolant within the engine oil cooler and, in turn, raising the viscosity of the engine oil within the engine oil system to raise the actual oil viscosity toward the target oil viscosity.

2. The engine oil system of claim 1, wherein the engine operating parameters comprise engine torque output.

3. The engine oil system of claim 1, wherein the engine operating parameters comprise engine oil temperature.

4. The engine oil system of claim 1, wherein the engine operating parameters comprise oil cooler coolant temperature.

5. The engine oil system of claim 1, wherein the oil viscosity sensor is disposed within a main oil gallery of the engine oil system.

6. A method of controlling viscosity of oil within an engine oil system comprising:

measuring the actual oil viscosity of the oil within the engine with an oil viscosity sensor;

monitoring engine performance with an electronic control module;

generating a desired target oil viscosity with the electronic control module which target oil viscosity changes continuously based upon the monitored engine performance;

routing the oil through an oil cooler when the measured viscosity is less than the desired target viscosity; and not routing the oil through an oil cooler when the measured viscosity exceeds the desired target viscosity.

7. The method of controlling viscosity of oil within an engine oil system of claim 6, wherein monitoring engine performance monitors engine torque output.

8. The method of controlling viscosity of oil within an engine oil system of claim 6, wherein monitoring engine performance monitors oil cooler coolant temperature.

9. The method of controlling viscosity of oil within an engine oil system of claim 6, wherein the target oil viscosity is set to minimize friction between lubricated engine components.

\* \* \* \* \*